(12) United States Patent
Bosel et al.

(10) Patent No.: US 7,967,794 B2
(45) Date of Patent: Jun. 28, 2011

(54) SAFETY NEEDLE ASSEMBLY

(75) Inventors: Christopher Bosel, Newark, DE (US);
Mark Sprinkle, Colora, MD (US)

(73) Assignee: Terumo Medical Corporation,
Somerset, NJ (US)

( * ) Notice: Subject to any disclaimer, the term of this patent is extended or adjusted under 35 U.S.C. 154(b) by 0 days.

(21) Appl. No.: 12/632,708

(22) Filed: Dec. 7, 2009

(65) Prior Publication Data
US 2010/0087784 A1 Apr. 8, 2010

Related U.S. Application Data

(62) Division of application No. 11/094,571, filed on Mar. 31, 2005, now Pat. No. 7,648,480.

(51) Int. Cl.
*A61M 5/32* (2006.01)
(52) U.S. Cl. ........................... 604/192; 604/110
(58) Field of Classification Search .................. 604/110, 604/164.08, 181, 187, 192, 198, 263
See application file for complete search history.

(56) References Cited

U.S. PATENT DOCUMENTS

| | | | |
|---|---|---|---|
| 3,658,061 A | 4/1972 | Hall | |
| 4,747,836 A | 5/1988 | Luther | |
| 4,820,277 A | 4/1989 | Norelli | |
| 4,838,871 A | 6/1989 | Luther | |
| 4,886,503 A | 12/1989 | Miller | |
| 4,909,791 A | 3/1990 | Norelli | |
| 4,909,792 A | 3/1990 | Norelli | |
| 4,915,696 A | 4/1990 | Feimer | |
| 4,944,731 A | 7/1990 | Cole | |
| 4,950,249 A | 8/1990 | Jagger et al. | |
| 4,966,591 A | 10/1990 | Yuen | |
| 4,982,842 A | 1/1991 | Hollister | |

(Continued)

FOREIGN PATENT DOCUMENTS

JP 2002-035128 2/2002

(Continued)

*Primary Examiner* — Theodore J Stigell
(74) *Attorney, Agent, or Firm* — Gael Diane Tisack, Esq.; Sills Cummis & Gross

(57) ABSTRACT

A safety needle assembly comprises a cannula holding member, a cannula fixed to the cannula holding member, and a safety device mounted on the cannula holding member. The cannula holding member includes one or more outwardly directed fins extending longitudinally along at least a portion of the cannula holding member. The safety device includes a collar adapted to be mounted on the cannula holding member and a sheath. The sheath possesses an interior bounded by a back wall and a pair of oppositely positioned side walls, and also includes an opening positioned opposite the back wall. The sheath is also provided with at least one fin engaging member connected to the back wall and extending from the back wall in a direction toward the opening. The fin engaging member is spaced from the side walls of the sheath. The sheath is pivotally connected to the collar to pivot in a closing direction toward the cannula so that during pivoting of the sheath in the closing direction the cannula passes through the opening in the sheath and is positioned in the interior of the sheath to be covered by the sheath, with the distal end portion of the at least one fin engaging member automatically engaging at least one of the fins on the cannula holding member when the cannula is positioned within the interior of the sheath to lock the sheath relative to the cannula holding member to prevent the sheath from being pivoted away from the cannula.

5 Claims, 9 Drawing Sheets

U.S. PATENT DOCUMENTS

| | | |
|---|---|---|
| 5,011,475 A | 4/1991 | Olson |
| 5,017,189 A | 5/1991 | Boumendil |
| 5,055,102 A | 10/1991 | Sitnik |
| 5,078,693 A | 1/1992 | Shine |
| 5,116,325 A | 5/1992 | Paterson |
| 5,135,509 A | 8/1992 | Olliffe |
| 5,139,489 A | 8/1992 | Hollister |
| 5,147,319 A | 9/1992 | Ishikawa et al. |
| 5,151,089 A | 9/1992 | Kirk, III et al. |
| 5,152,751 A | 10/1992 | Kozlowski |
| 5,154,285 A | 10/1992 | Hollister |
| 5,188,611 A | 2/1993 | Orgain |
| 5,207,653 A | 5/1993 | Janjua et al. |
| 5,232,454 A | 8/1993 | Hollister |
| 5,232,455 A | 8/1993 | Hollister |
| 5,242,417 A | 9/1993 | Paudler |
| 5,312,367 A | 5/1994 | Nathan |
| 5,312,369 A | 5/1994 | Arcusin et al. |
| 5,389,083 A | 2/1995 | McCarthy |
| 5,405,332 A | 4/1995 | Opalek |
| 5,445,619 A | 8/1995 | Burns |
| 5,486,163 A | 1/1996 | Haynes |
| 5,490,841 A | 2/1996 | Landis |
| 5,496,274 A | 3/1996 | Graves et al. |
| 5,509,907 A | 4/1996 | Bevilacqua |
| 5,584,816 A | 12/1996 | Gyure et al. |
| 5,599,313 A | 2/1997 | Gyure et al. |
| 5,599,318 A | 2/1997 | Sweeney et al. |
| 5,615,771 A | 4/1997 | Hollister |
| 5,632,732 A | 5/1997 | Szabo et al. |
| 5,643,219 A | 7/1997 | Burns |
| 5,662,617 A | 9/1997 | Odell et al. |
| 5,665,075 A | 9/1997 | Gyure et al. |
| 5,669,889 A | 9/1997 | Gyure et al. |
| 5,672,161 A | 9/1997 | Allen et al. |
| 5,693,022 A | 12/1997 | Haynes |
| 5,704,920 A | 1/1998 | Gyure |
| 5,733,265 A | 3/1998 | Bachman et al. |
| 5,735,827 A | 4/1998 | Adwers et al. |
| 5,738,665 A | 4/1998 | Caizza et al. |
| 5,746,726 A | 5/1998 | Sweeney et al. |
| 5,807,351 A | 9/1998 | Kashmer |
| 5,814,018 A | 9/1998 | Elson et al. |
| 5,836,920 A | 11/1998 | Robertson |
| 5,868,716 A | 2/1999 | Sweeney et al. |
| 5,891,103 A | 4/1999 | Burns |
| 5,910,130 A | 6/1999 | Caizza et al. |
| 5,913,846 A | 6/1999 | Szabo |
| 5,919,165 A | 7/1999 | Benson |
| 5,925,032 A | 7/1999 | Clements |
| 5,993,426 A * | 11/1999 | Hollister ................. 604/192 |
| 6,120,482 A | 9/2000 | Szabo |
| 6,156,012 A | 12/2000 | Nathan |
| 6,186,325 B1 | 2/2001 | Schmidt et al. |
| RE37,110 E | 3/2001 | Hollister |
| 6,413,243 B1 | 7/2002 | Geist |
| 6,582,397 B2 * | 6/2003 | Alesi et al. ................. 604/110 |
| 6,695,819 B2 | 2/2004 | Kobayashi |
| 6,719,737 B2 | 4/2004 | Kobayashi |
| 2006/0149188 A1 * | 7/2006 | Simas, Jr. ................. 604/110 |

FOREIGN PATENT DOCUMENTS

JP      2002-102344      4/2002

* cited by examiner

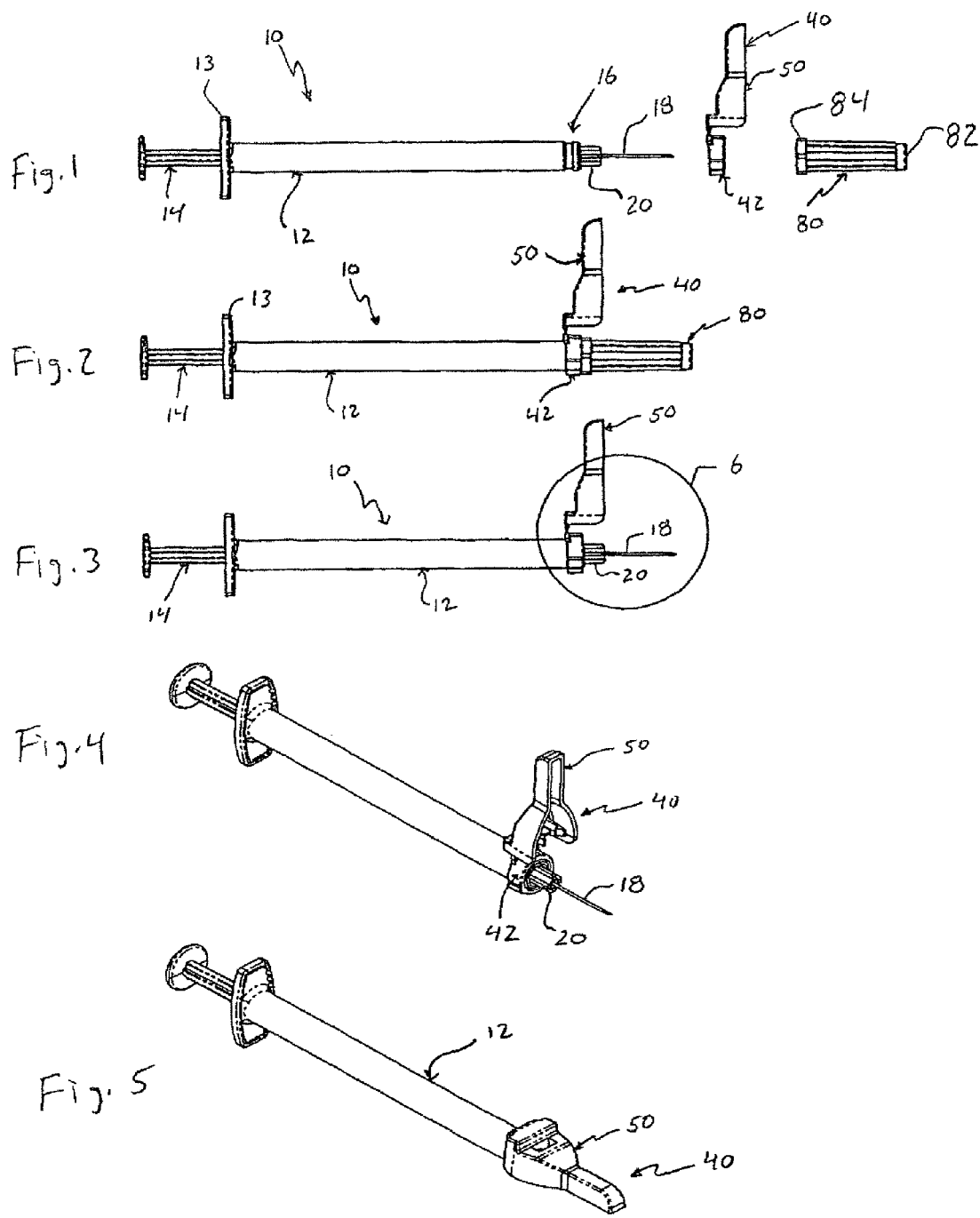

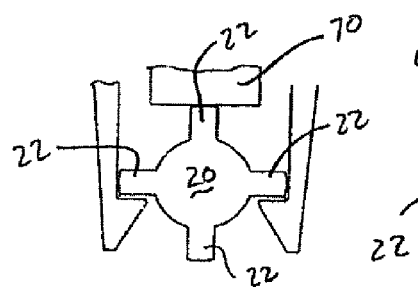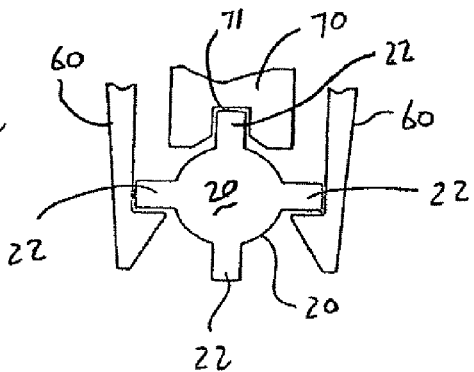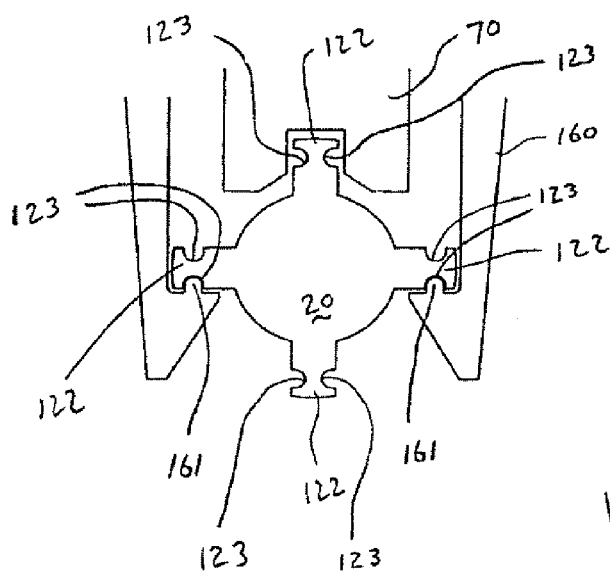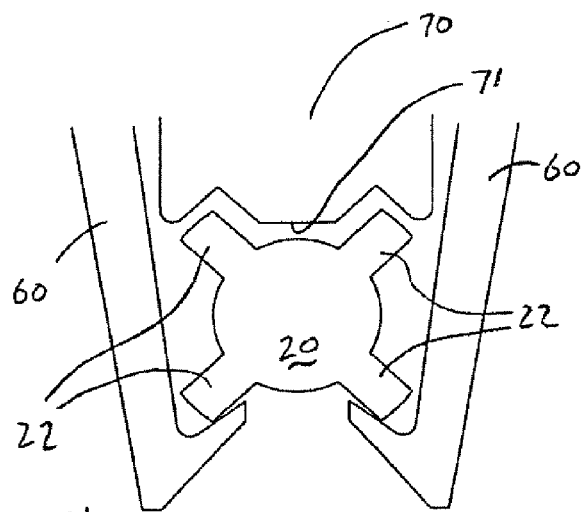

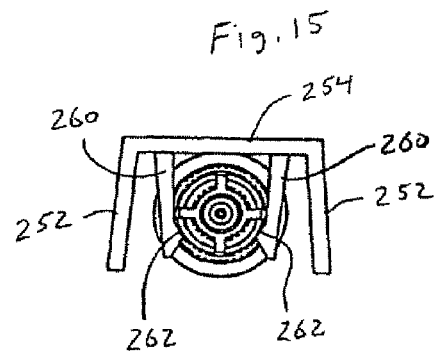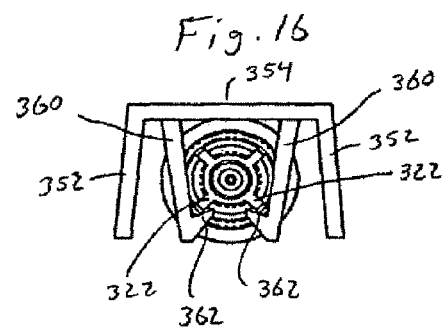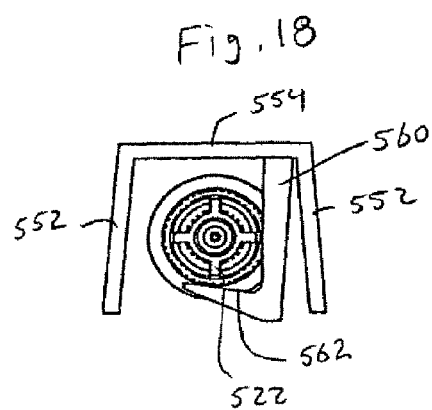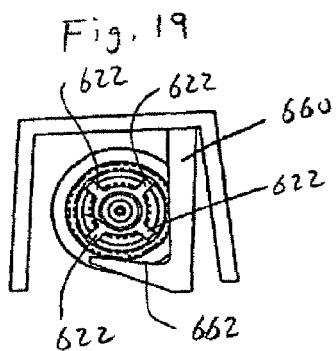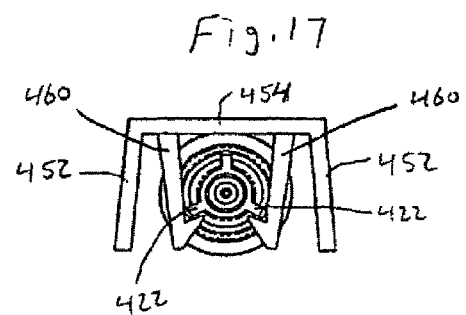

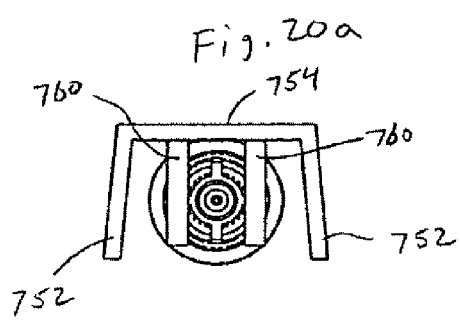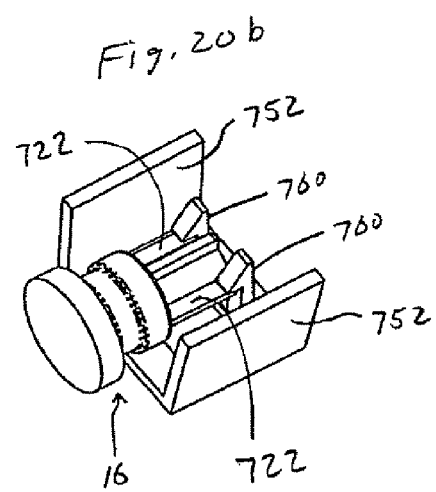

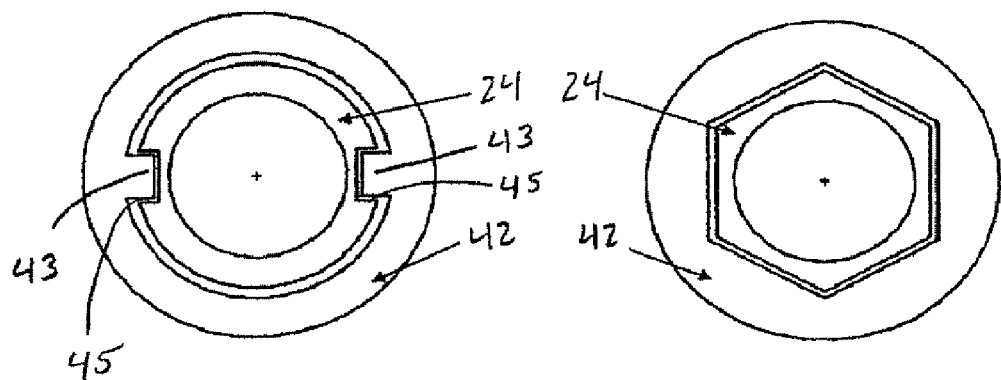
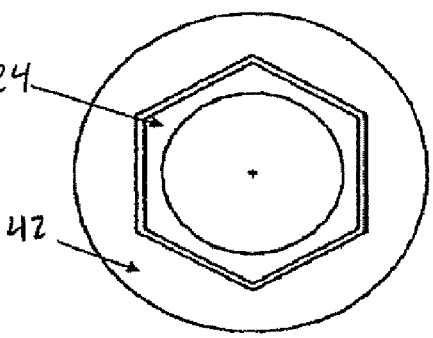
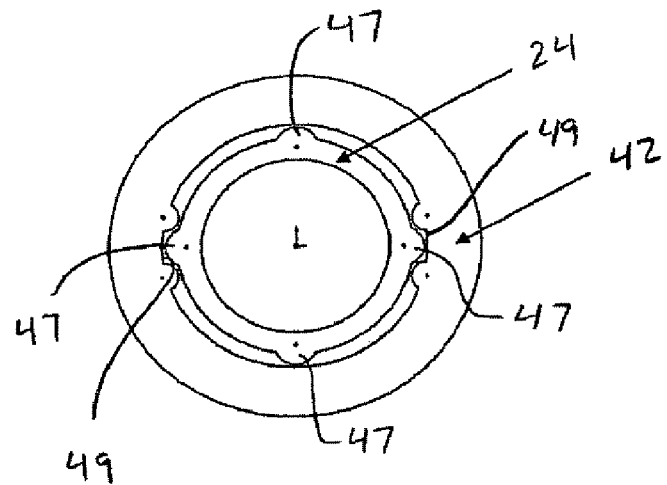

SAFETY NEEDLE ASSEMBLY

CROSS REFERENCE TO RELATED APPLICATIONS

The present application is a divisional of U.S. patent application Ser. No. 11/094,571, filed on Mar. 31, 2005, now U.S. Pat. No. 7,648,480, the contents of which are hereby incorporated by reference in their entirety.

FIELD OF THE INVENTION

The present invention pertains to needle assemblies used in connection with various medical procedures. More particularly, the present invention relates to a safety needle assembly in which a safety device is operable to cover a cannula.

BACKGROUND DISCUSSION

Needle assemblies are used in different medical instruments in connection with a wide array of medical procedures. It is desirable for the needle assembly to be constructed in a way that minimizes the potential for a user such as a healthcare worker to come in contact with the cannula of the used needle assembly. One known type of arrangement for addressing this concern involves the use of a rigid cylindrical cap which is positioned over the cannula and engages the hub to which the cannula is connected. During use, the cylindrical cap is removed to expose the cannula. After using the syringe/needle assembly for its intended procedure, the cylindrical cap must be once again mounted on the hub to cover the used cannula. Oftentimes, the healthcare professional tries to replace the cylindrical cap on the needle assembly (e.g., in connection with a syringe) by "scooping" the cylindrical cap with the needle assembly. This may not be an easy or effective technique for repositioning the protective cap on the syringe/needle assembly. The cap can also become accidentally dislodged from the needle assembly, thus exposing the used cannula and presenting a potential danger.

Another proposal presented in U.S. Pat. No. RE 37,110 involves the use of a housing pivotally connected to a base which is associated with the needle assembly. The housing is adapted to be pivoted to a covering position in which the housing covers the cannula. In addition, a locking mechanism is provided between the housing and the base to lock the housing in the covering position relative to the cannula.

U.S. Pat. No. 5,662,617 discloses other proposals, some of which involve a sheath pivotally connected to a needle hub mount that is adapted to be mounted on a needle hub. In one disclosed embodiment, the side walls of the sheath are adapted to engage riblets on the needle hub when the sheath is pivoted toward the cannula. The engagement between the sheath side walls and the riblets on the needle hub is releasable to permit repeated releasable closure of the sheath.

SUMMARY

According to one aspect, a safety needle assembly comprises a cannula holding member possessing a distal end portion comprising a hub, a cannula fixed to the hub and possessing a beveled distal end projecting beyond the distal end of the hub, with the hub comprising a plurality of outwardly directed fins extending longitudinally along at least a portion of the hub, and a sheath possessing a generally U-shaped cross-section and an interior bounded by a back wall and a pair of oppositely positioned side walls. The sheath also comprises an opening positioned opposite the back wall, with the opening extending along at least a portion of a longitudinal extent of the sheath. The sheath also includes at least one fin engaging member connected to the back wall and extending from the back wall of the sheath in a direction toward the opening, the at least one fin engaging member being spaced from both side walls of the sheath and possessing a distal end portion. An annular collar is separate from the cannula holding member and is mounted on the cannula holding member, and the sheath is pivotally connected to the collar to pivot in a closing direction toward the cannula so that during pivoting of the sheath in the closing direction the cannula passes through the opening in the sheath and is positioned in the interior of the sheath so as to be covered by the sheath, with the distal end portion of the at least one fin engaging member automatically engaging at least one of the fins on the hub when the cannula is positioned within the interior of the sheath to lock the sheath relative to the hub to prevent the sheath from being pivoted away from the cannula.

According to another aspect, a safety needle assembly comprises a cannula holding member, and a cannula fixed to the cannula holding member and possessing a distal end projecting beyond the distal end of the cannula holding member, with the cannula holding member comprising at least two fins, each of the fins projecting outwardly away from the cannula holding member and extending along at least a portion of a longitudinal extent of the cannula holding member. A sheath comprises a back wall, oppositely positioned side walls, and an opening positioned opposite the back wall, with the opening extending along at least a portion of a longitudinal extent of the sheath. At least one arm is connected to the back wall of the sheath and extends in a cantilever manner from the back wall of the sheath in a direction toward the opening. The sheath is provided on the cannula holding member and is pivotable relative to the cannula holding member to pivot toward the cannula from one position in which the cannula is exposed to another position in which the sheath covers the cannula and the distal end portion of the at least one arm engages at least one of the fins to prevent the sheath from being pivoted back toward the one position.

In accordance with another aspect, a safety needle assembly comprises a cannula holding member, and a cannula fixed to the cannula holding member and possessing a distal end projecting beyond the distal end of the cannula holding member, wherein the cannula holding member comprises a fin region at which are located a plurality of fins, with each of the fins projecting outwardly away from the cannula holding member and extending along at least a portion of the longitudinal extent of the cannula holding member. A collar is mounted on the cannula holding member and at least a portion of the fin region of the cannula holding member is located between the collar and the distal end of the cannula holding member. The assembly also includes a sheath comprising an interior bounded by a back wall and a pair of side walls, with the sheath being provided with an opening positioned opposite the back wall, wherein the opening extends along at least a portion of the longitudinal extent of the sheath. At least one arm is connected to the back wall of the sheath and extends away from the back wall toward the opening. The sheath is pivotally connected to the collar to pivot relative to the cannula holding member in a direction toward the cannula to cause the distal end portion of the at least one arm to engage the fin region of the cannula holding member to automatically lock the sheath in a cannula covering position in which the cannula is located within the interior of the sheath so that the sheath is prevented from pivoting away from the cannula.

According to another aspect, a safety device is configured to be attached to a needle assembly which comprises a cannula and a cannula holding member from which extends at least one longitudinally extending fin, with the cannula being mounted at the cannula holding member and possessing a distal end projecting beyond an end of the cannula holding member. The safety device comprises an annular collar adapted to be mounted on the cannula holding member, and a sheath that comprises an interior bounded by a back wall and a pair of oppositely positioned side walls. The sheath also includes an opening located opposite the back wall and extending along at least a portion of the longitudinal extent of the sheath. The sheath also comprises at least one arm connected to the back wall, with the arm extending away from the back wall in a direction toward the opening. The at least one arm is positioned in spaced relation to both side walls of the sheath. In addition, a connection means is provided for pivotally connecting the sheath to the collar so that when the collar is mounted on the cannula holding member the sheath is pivotable toward the cannula to a locked cannula covering position in which the cannula is positioned in the interior of the sheath and the distal end portion of the at least one arm engages the at least one fin on the cannula holding member to lock the sheath relative to the cannula holding member to prevent the sheath from being pivoted away from the cannula.

Another aspect involves a method of covering a cannula fixed to a cannula holding member. The method comprises pivoting a sheath that is pivotally mounted on the cannula holding member, wherein the cannula is fixed to the cannula holding member so that a beveled distal end of the cannula projects beyond a distal end of the cannula holding member. The cannula holding member comprises at least one outwardly directed and longitudinally extending fin, and the sheath comprises an interior bounded by a back wall, a pair of oppositely positioned side walls and an opening located opposite the back wall with the opening extending along at least a portion of a longitudinal extent of the sheath. The sheath also comprises at least one arm in the interior of the sheath which is connected to the back wall, extends away from the back wall in a direction toward the opening and is positioned in spaced relation to both side walls of the sheath. The sheath is pivoted toward the cannula to cause the beveled distal end of the cannula to be positioned in the interior of the sheath and to cause a distal end portion of the at least one arm to engage the at least one fin on the cannula holding member to lock the sheath in a cannula covering position relative to the cannula holding member and prevent the sheath from being pivoted away from the cannula.

BRIEF DESCRIPTION OF THE DRAWING FIGURES

FIG. 1 is an exploded side view of a fluid transfer device embodying one version of the safety needle assembly, including the safety device, of the present invention.

FIG. 2 is a side view of the fluid transfer device shown in FIG. 1 in an assembled state.

FIG. 3 is a side view of the fluid transfer device shown in FIG. 2, but with the protector removed.

FIG. 4 is a perspective view of the fluid transfer device shown in FIG. 3 illustrating the sheath in the open position.

FIG. 5 is a perspective view of the fluid transfer device shown in FIG. 4 with the sheath in the closed cannula covering position.

Figure 8B:
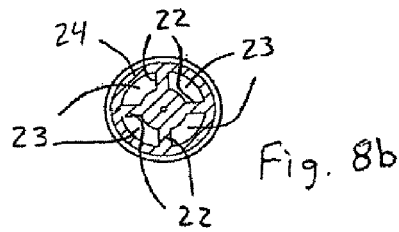
Figure 8A:
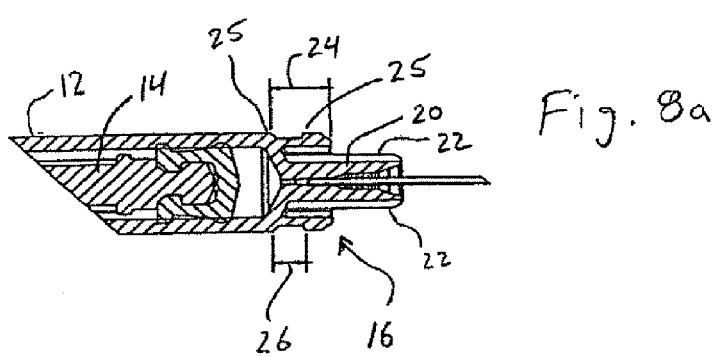

FIG. 8*a* is an enlarged cross-sectional view of the distal end portion of the fluid transfer device shown in FIG. 1 illustrating the needle assembly.

FIG. 8*b* is a cross-sectional view through the skirt region of the cannula holding member shown in FIG. 8*a*.

Figure 9:
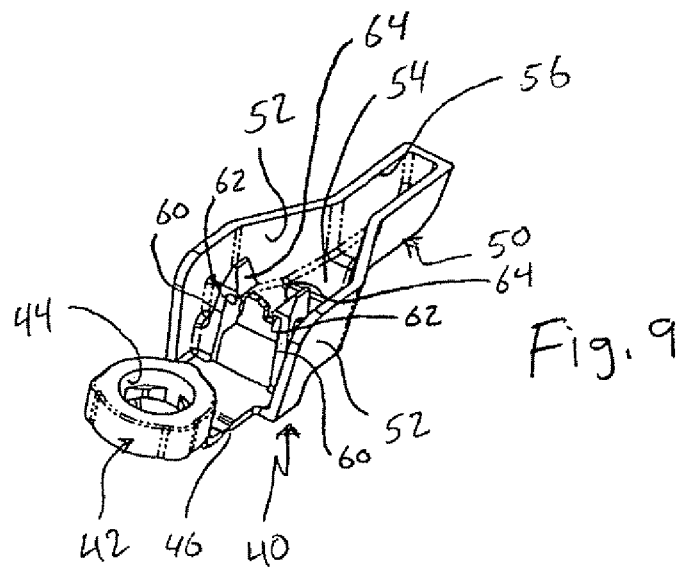

FIG. 9 is an enlarged perspective view of the safety device shown in FIG. 1.

Figure 10:
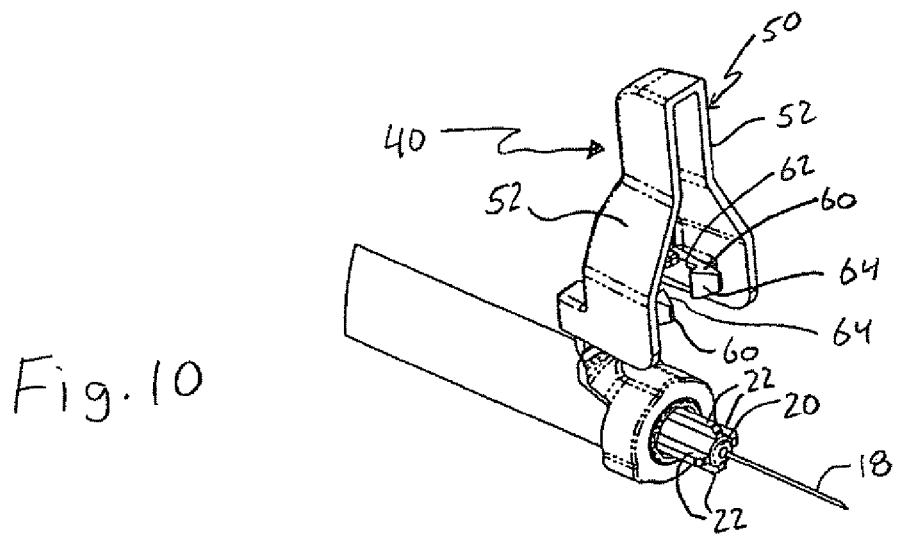

FIG. 10 is an enlarged perspective view of the safety device mounted on the cannula holding member, with the sheath in the open position.

Figure 11:
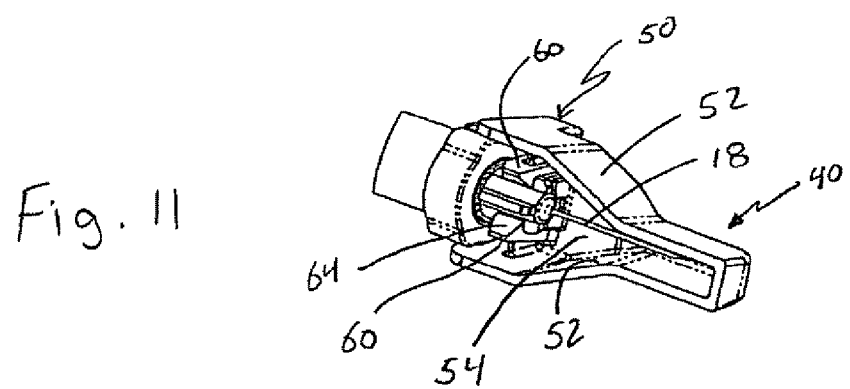

FIG. 11 is an enlarged bottom perspective view of the safety device and cannula holding member shown in FIG. 10, but with the sheath in the closed cannula covering position.

FIG. 12*a* is a simplified illustration of a portion of the safety needle assembly illustrating the engagement of the fin engaging members with the fins when the sheath is in the closed cannula covering position and depicting the stop rib that contacts one of the fins to prevent excessive pivoting movement of the sheath.

FIG. 12*b* is a simplified illustration of a portion of the safety needle assembly similar to FIG. 12*a*, but illustrating a different arrangement of the fins and a different configuration for the recess in the stop rib that contacts the fins FIG. 13 is a simplified illustration similar to FIG. 12*a*, but illustrating a different configuration for the rib that prevents excessive pivoting movement of the sheath.

FIG. 14 is a view similar to FIG. 12*a*, but illustrating a different embodiment of the fin engaging members and the fins.

FIG. 15 is a simplified illustration of a portion of the cannula holding member and safety device illustrating an alternative embodiment of the fin engaging members.

FIG. 16 is a simplified illustration of a portion of the cannula holding member and safety device illustrating an alternative arrangement of the fins together with a modified version of the fin engaging members.

FIG. 17 is a simplified illustration of a portion of the cannula holding member and safety device illustrating an alternative arrangement of the fins together with a modified version of the fin engaging members.

FIG. 18 is a simplified illustration of a portion of the cannula holding member and safety device according to another embodiment in which a single fin engaging member is provided.

FIG. 19 is a simplified illustration of a portion of the cannula holding member and safety device similar to FIG. 18, but with different positioning of the fins.

FIG. 20*a* is a simplified illustration of a portion of a cannula holding member and safety device according to another embodiment.

FIG. 20*b* is a perspective view of the embodiment of the cannula holding member and safety device shown in FIG. 20*a*.

Figure 21:
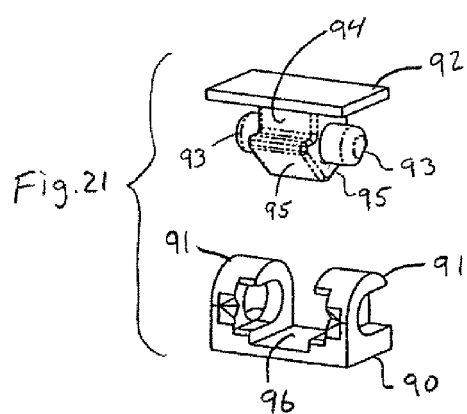

FIG. 21 is a perspective view of one embodiment of a multi-piece hinge for pivotally connecting the sheath to the collar.

Figure 22:
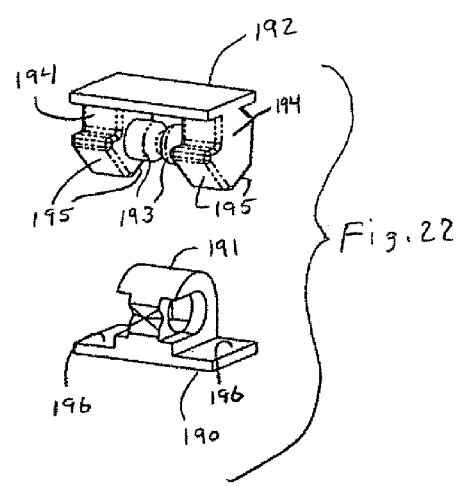

FIG. 22 is a perspective view of another embodiment of the multi-piece hinge for connecting the sheath to the collar.

Figure 23:
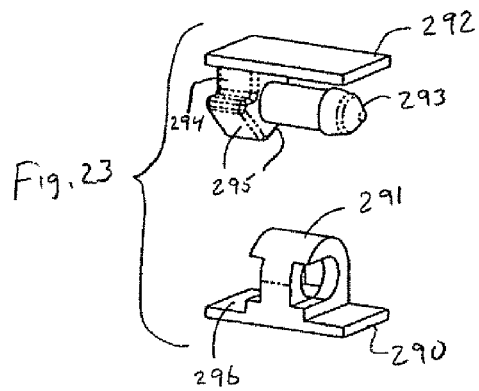

FIG. 23 is a perspective view of another embodiment of the multi-piece hinge for connecting the sheath to the collar.

Figure 24:
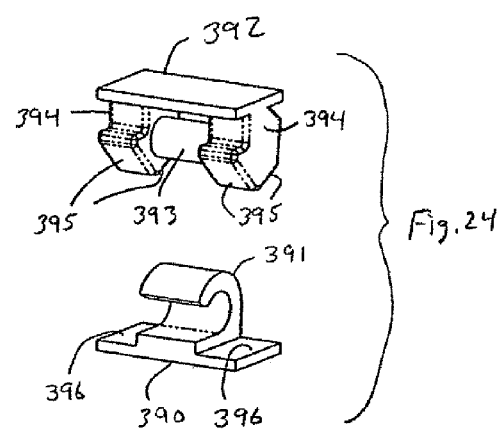

FIG. 24 is a perspective view of another embodiment of the multi-piece hinge for connecting the sheath to the collar.

FIG. 25 is a cross-sectional view of a portion of the cannula holding member and safety device illustrating one arrangement for fixing the position of the collar on the skirt of the cannula holding member.

FIG. 26 is a cross-sectional view of a portion of the cannula holding member and safety device illustrating another arrangement for fixing the position of the collar on the skirt region of the cannula holding member.

FIG. 27 is a cross-sectional view of a portion of the cannula holding member and safety device illustrating the connection between the skirt region of the cannula holding member and the collar for purposes of providing a ratchet-type of rotation of the collar.

Figure 28:
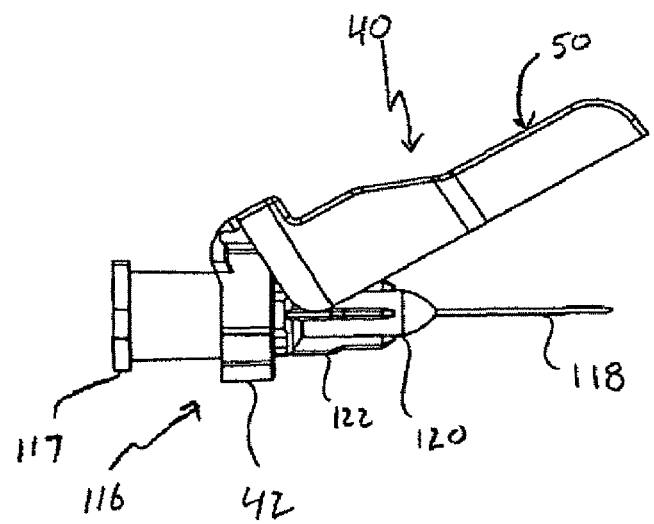

FIG. 28 is a side view of a safety needle assembly in which the safety device is mounted on an alternative embodiment of the cannula holding member, with the sheath being illustrated in the open position.

Figure 29:
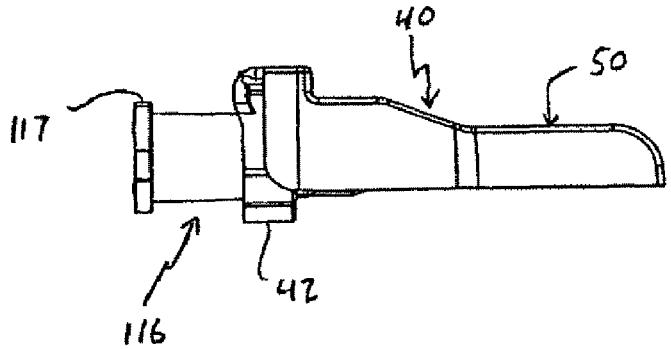

FIG. 29 is a side view of safety needle assembly shown in FIG. 28, but with the sheath in the closed cannula covering position.

Figure 30:
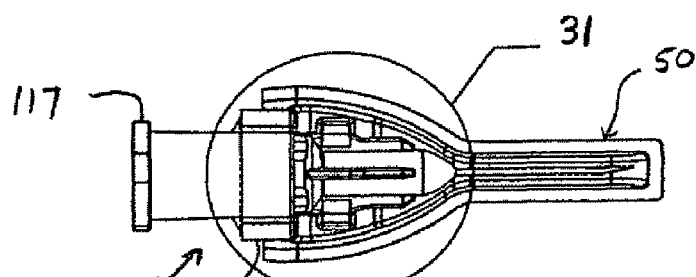

FIG. 30 is a bottom view of the safety needle assembly shown in FIG. 29.

Figure 31:
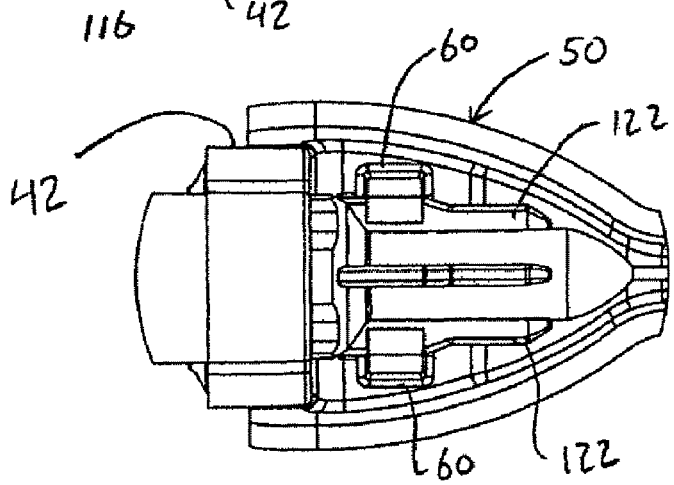

FIG. 31 is an enlarged bottom view of the circled portion of the safety needle assembly shown in FIG. 30.

DETAILED DESCRIPTION

The safety needle assembly described herein is adapted to be used in connection with or form a part of a fluid transfer device. As described below in more detail, the safety needle assembly can be formed as a fixed and integral (unitary) part of the fluid transfer device, or can be separate from and connectable to the fluid transfer device.

FIG. 1 illustrates a fluid transfer device embodying the safety needle assembly according to one embodiment. In this embodiment, the fluid transfer device is in the form of a syringe 10 and includes a hollow syringe barrel 12 which receives a plunger 14 capable of sliding relative to the syringe barrel 12. The proximal end of the syringe barrel is provided with a finger flange 13.

A hub 20 is provided at the distal end of the syringe barrel 12 and a cannula 18 is fixed in place at the hub 20. The cannula 18 can be connected to the hub 20 in a typical manner such as through the use of an epoxy. The cannula 18 includes a proximal end portion fixed to the hub 20 and a distal end portion provided with a bevel to form a beveled distal end portion. A lumen passing through the cannula 18 communicates with the interior of the syringe barrel. The hub 20 together with a distal end portion of the syringe barrel 12 form a cannula holding member 16.

In the illustrated embodiment, a safety device 40 is adapted to be mounted on the cannula holding member 16. In addition, a protector 80 can optionally be provided for being positioned over the cannula 18 in covering relation thereto, with the proximal end portion of the protector 80 frictionally engaging the hub 20 to removably retain the protector in place on the cannula holding member 16.

Figure 6:
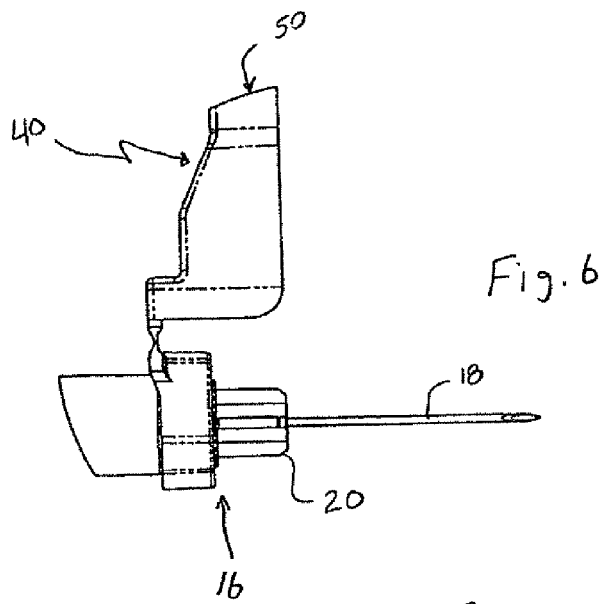
FIG. 6 is an enlarged view of the circled portion of the fluid transfer device shown in FIG. 3.
Figure 7:
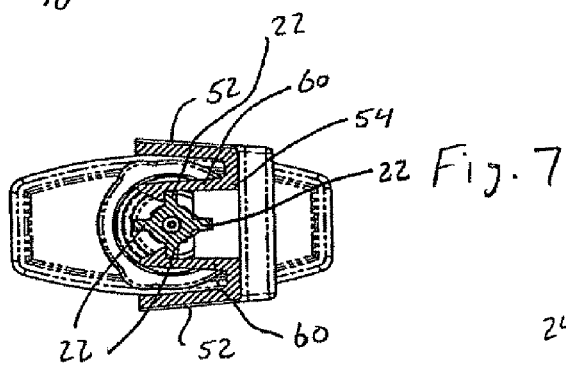
FIG. 7 is a cross-sectional view of the safety needle assembly when the sheath is in the closed cannula covering position.

As better seen in the FIG. 7 cross-sectional view, the hub 20 is provided with a plurality of fins 22 forming fixed projections. That is, the fins 22 are immovable relative to the hub 20. The fins 22 are located in a fin region of the hub 20 and project radially outwardly from the hub. The fins 22 also extend longitudinally along at least a portion of the longitudinal extent of the hub. The fins 22 are integrally formed with the hub so that the fins 22 and the hub 20 together form a one-piece part. The purpose associated with the fins 22 (fin region) in connection with the disclosure here will be described below in more detail. The fins 22 can also serve to provide a mating surface that is frictionally engaged by the protector 80 when the protector 80 is positioned in covering relation to the cannula 18.

The fins 22 of the needle assembly 16 can be evenly spaced apart around the outer circumferential surface of the hub 20 in the manner shown in FIG. 10. Alternatively, the fins can be unevenly spaced apart. As illustrated in FIG. 10, the hub 20 can be provided with four fins. When the hub 20 is provided with four fins evenly-spaced apart around the outer circumferential surface of the hub 20, adjacent pairs of fins are spaced apart ninety degrees from one another. In such a version, two of the fins can be positioned in alignment with the finger flange 13 of the syringe barrel 12, while the other two fins are perpendicular to the finger flange of the barrel.

As an alternative, when four fins 22 are provided on the hub 20, the fins can be shifted 45 degrees rotationally from the positions described above so that each of the fins 22 is shifted 45 degrees out of alignment with the finger flange 13 of the syringe barrel 12. The specific number of fins is not limited to four as other numbers of fins can be provided consistent with the operational characteristics of the safety needle assembly as described in more detail below. By way of example, the hub 20 can be provided with three fins spaced apart at 120 degree rotational intervals from one another, with one of the fins being in alignment with the finger flange 13 of the syringe barrel 12.

As best seen in FIG. 8a, the cannula holding member 16 includes a skirt or skirt region 24. This skirt region 24 is generally formed as a hollowed-out section at the distal end part of the syringe barrel. The skirt 24 generally forms an extension that encircles or surrounds the fins 22 along at least a portion of the longitudinal extent of the fins 22. The portion of the skirt 24 that encircles or surrounds the fins 22 is fixed to or integrally formed in one piece with the fins 22. Circumferentially spaced apart gaps or openings 23 are thus defined between the adjacent pairs of the fins as shown in FIG. 8b. The distal end of the skirt 24 can serve as a stopping mechanism against which the protector 80 abuts when the protector 80 is positioned over the hub 20 in covering relation to the cannula 18.

Hollowing-out the end of the syringe barrel to produce the skirt 24 reduces the material thickness in the region of the skirt 24 so that the part can be more easily molded. The thinned wall forming the skirt 24 is relatively rigid near the proximal end (i.e., closer to the finger flange 13) and in the regions at which the skirt region 24 is fixed to or integrally formed with the fins 22, but is relatively flexible toward the distal end of the thinned wall in the portions spaced from the fins 22 (i.e., between the fins). This can help facilitate assembly of the safety device 40 to the needle assembly 16.

The cannula holding member 16 also includes an annular recessed region 26 as shown in FIG. 8a. In the illustrated embodiment, the annular recessed region 26 is spaced proximally a relatively short distance from the distal end of the skirt region 24. The recessed region 26 is also positioned so that at least a portion of the recessed region overlies the fin region at which are located the fins 22. As described in more detail below, the annular recessed region 26 serves as a region for mounting the safety device 40 on the needle assembly 16.

As best seen in FIG. 8a, the outer diameter of the annular recessed region 26 is smaller than the outer diameter at both axial ends of the annular recessed region 26. Stated differently, the outer diameter of the portions 25 of the skirt 24 immediately adjoining the axial ends of the annual recessed region 26 is greater than the outer diameter of the annular recessed region 26.

As generally shown in FIG. 1, the protector 80 is formed as an elongated cylindrical hollow member having a distal end 82 and a proximal end 84. The protector 80 is open at the proximal end 84 and preferably closed at the distal end 82.

The exterior surface of the protector 80 can be provided with longitudinal ribs to facilitate gripping by the user. When the protector 80 is positioned in the manner shown in FIG. 2 so that the protector 80 covers the cannula 18, the proximal end 84 of the protector 80 abuts the distal end of the skirt 24 so that the protector 80 cannot be advanced any further.

Features associated with the safety device 40 are best seen in FIG. 9. The safety device 40 includes a collar 42 and a sheath 50. The collar 42 is adapted to be mounted on the cannula holding member 16. The sheath 50 is pivotally connected to the collar 42 so that the sheath can be pivoted relative to the collar 42. This pivoting movement can be achieved by connecting the sheath 50 to the collar 42 by way of a hinge. By way of example, the hinge can be in the form of a living hinge 46 which connects the proximal end of the sheath 50 to an outwardly extending tab on the collar 42. The safety device 40 together with the cannula holding member 16 and the cannula 18 (and also with the optional protector 80 when used) forms a safety needle assembly.

The collar 42 is provided with a centrally located through hole 44 so that the collar 42 possesses an annular shape. The collar 42 is adapted to be mounted on the cannula holding member 16 by virtue of being seated in the annular recessed region 26. The collar 42 preferably possesses an inner diameter that is less than the outer diameter of the axial end portions 25 adjoining the annular recessed region 26. In this way, when the collar 42 is positioned in the annular recessed region 26, the collar 42 is axially held in place and inhibited or prevented from axially sliding off the skirt 24. The inner diameter of the collar 42 can be equal to, slightly greater than or slightly less than the outer diameter of the recessed region 26.

As the collar 42 is mounted on the cannula holding member 16, the somewhat flexible skirt 24 is slightly deformed so that the collar 42 can be slid axially to the recessed region 26. As mentioned above, the axial end portions 25 adjoining the annular recessed region 26 are configured to prevent the collar 42 from inadvertently being axially displaced from the recessed region 26. It is to be understood that the collar 42 can be configured in other ways to inhibit or prevent the collar from axially sliding off the cannula holding member 16. For example, the inside surface of the collar 42 could be provided with an inwardly directed ridge adapted to be seated in the annular recessed region 26, in this arrangement, the inner diameter defined by the inwardly directed ridge would be less than the outer diameter of the axial end portions 25 adjoining the annular recessed region 26 so that the collar 42 does not slide axially off the recessed region 26. Once again, the inner diameter of the inwardly extending ridge can be equal to, slightly greater than or slightly less than the outer diameter of the recessed region 26 on the cannula holding member 16. Also, the inwardly directed ridge may be formed as a continuous uninterrupted annular ridge, or can be formed as a plurality of separated segments, each extending along a portion of the inner circumference of the collar. Other arrangements are also possible for configuring the collar 42 and/or the cannula holding member 16 so that the collar is inhibited or prevented from axially sliding off the cannula holding member 16 or being axially displaced from the recessed region 26.

The sheath 50 forming a part of the safety device has a somewhat U-shaped cross-section as shown in FIG. 9. The sheath 50 comprises a pair of side walls 52, 52 and a back wall 54 extending between and connecting the two side walls 52, 52. FIG. 9 shows that the width dimension (i.e., the distance between the side walls 52, 52) of the sheath 50 varies along the longitudinal extent of the sheath 50. However, the sheath 50 need not have this particular configuration, as the width of the sheath 50 may vary to a greater or lesser extent than that shown, or may be constant along its entire length.

As further shown in FIG. 9, the sheath 50 is configured to include an opening 56 located opposite the back wall 54. The opening 56 extends along at least a portion of the longitudinal extent of the sheath 50. In the illustrated embodiment, the opening 56 extends along the entire longitudinal extent of the sheath 50 so that the sheath 50 is open along its entire front side. The opening 56 opens into the interior of the sheath 50 that is bounded by the side walls 52, 52 and the back wall 54.

As described below in more detail, during use of the safety needle assembly, the sheath 50 is adapted to be pivoted towards the cannula 18 so that the cannula passes through the opening 56 of the sheath and into the interior of the sheath, whereby the cannula 18 is covered by the sheath 50. It can thus be seen that the configuration of the opening and the extent to which the opening extends along the sheath 50 can vary, so long as the cannula 18 is capable of passing through the opening in the sheath 50 and entering the interior of the sheath when the sheath 50 is pivoted towards the cannula.

As best seen in FIGS. 9-11, the sheath 50 also comprises a pair of fin engaging members 60. Each of the fin engaging members 60 is preferably spaced from and movable relative to the sidewalls 52, 52 of the sheath 50. In the illustrated embodiment, both of the fin engaging members 60, 60 are in the form of cantilever arms connected to the back wall 54 of the sheath 50. The fin engaging members 60, 60 can be configured to extend from the back wall at a slight inwardly angle (i.e., away from the adjoining side wall 52) so that instead of extending perpendicular to the back wall, the two fin engaging members 60, 60 are angled slightly towards one another.

The distal end portion of each fin engaging member 60, 60 is preferably provided with a fin engaging part. In the illustrated embodiment, the fin engaging part is in the form of an inwardly directed shoulder 62, 62 so that the distal end portion of each fin engaging member 60, 60 is generally hook-shaped. As described below in more detail, the shoulder 62, 62 on each of the fin engaging members 60, 60 is adapted to engage one of the fins on the hub 20 of the cannula holding member 16 when the sheath 50 is pivoted from the open (cannula uncovering) position shown in FIG. 10 to the closed (cannula covering) position shown in FIG. 11. As generally illustrated in FIGS. 9-11, the distal end portion of each fin engaging member 60, 60 is also provided with an inclined surface 64, 64.

FIG. 10 illustrates the safety device 40 attached to the cannula holding member 16. In the position illustrated in FIG. 10, the sheath 50 is spaced from the cannula 18 so that the cannula 18 is exposed (uncovered). The sheath 50 is adapted to be pivoted in a closing direction towards the cannula 18 to the closed cannula covering position shown in FIG. 11. As the sheath 50 is pivoted towards the cannula 18, the inclined surface 64, 64 of each of the fin engaging members 60, 60 contacts one of the fins 22 on the hub 20 of the cannula holding member 16. Continued pivoting movement of the sheath 50 in the closing direction causes the fin engaging members 60, 60 to spread apart slightly due to the contact of the inclined surfaces 64, 64 with the fins 22. With further pivoting movement of the sheath 50 toward the cannula 18, the hook-shaped distal end portions of the fin engaging members 60, 60 move past the fins 22, whereupon the resiliency of the fin engaging members 60, 60 causes the fin engaging members 60, 60 to move slightly inwardly towards one another to the position shown in FIG. 11. In this closed cannula covering position, the distal end portions of the fin engaging members 60, 60 engage respective fins 22, thus locking the sheath in the closed cannula covering position. The engagement of the fin engaging members 60, 60 with the respective fins 22, 22 is also shown in the cross-section of FIG. 7.

Thus, as the sheath 50 is pivoted towards the cannula 18, the sheath is automatically locked in the closed cannula covering position by virtue of a portion of the fin engaging members 60, 60 engaging the respective fins 22, 22. Automatic locking refers to the fact that the pivoting movement of the sheath 50 sufficiently in the closing direction toward the cannula to the position shown in FIG. 11 results in locking of the sheath in the closed cannula covering position without the need for further action by the user. In addition, the automatic locking of the sheath 50 in the cannula covering position shown in FIG. 11 is permanent in that there is no structure to effect unlocking of the sheath and the cannula will remain covered by the sheath under application of normal forces encountered during subsequent handling and disposal.

Of course, it is to be understood that if the protector 80 shown in FIGS. 1 and 2 is used, the protector 80 will have been previously removed prior to use of the fluid transfer device (e.g., syringe). Thus, the protector 80 will not be present when the sheath 50 is pivoted toward the cannula.

FIG. 12a schematically illustrates the fin engaging members 60, 60 engaged with the fins 22, 22 on the hub 20 of the cannula holding member 16. The illustration in FIG. 12a is similar to the illustration in FIG. 7, except that various details have been omitted for purposes of clearly illustrating the engagement of the fin engaging members 60, 60 with the fins 22, 22 when the sheath 50 is in the locked cannula covering position.

As seen in FIG. 12a, the sheath 50 is also provided with a rib 70. This rib 70 serves as a stop for preventing further significant pivoting movement of the sheath 50 in the closing direction once the fin engaging members 60, 60 have engaged respective fins 22, 22. The reason for this is to avoid contact of the sheath 50 with the cannula 18. More specifically, once the fin engaging members 60, 60 have engaged the respective fins 22, 22 as shown in FIG. 12a, the stop rib 70 contacts another one of the fins 22 to prevent further pivoting movement of the sheath in the closing direction. This is helpful from the standpoint that further significant pivoting movement of the sheath 50 beyond the position where the fin engaging members 60, 60 engage the fins 22, 22 might cause the sheath 50 to come in contact with the cannula 18 and cause splashing or spraying of fluid (e.g., blood) that may be on the cannula.

As seen in FIG. 12a, the stop rib 70 can also be configured to include a recess 71 that receives one of the fins 22. The recess in the stop rib can have a shape or configuration different than that shown in FIG. 12a depending upon, for instance, the arrangement of the fins 22 on the hub 20. By way of example, as shown in FIG. 12b, when the fins are rotationally offset 45 degrees from the position shown in FIG. 12a, the recess 71 in the stop rib 70 can be made wider and differently shaped so that the recess is able to accommodate two of the fins 22 as the sheath is pivoted in the closing direction. The recess 71 in the rib shown in FIG. 12b is deeper at the ends to accommodate end portions of the fins 22 oriented in the illustrated manner. Of course, as illustrated in FIG. 13, the stop rib 70 can be configured without a recess so that the end surface of the stop rib 70 contacts the end surface of one (or two) of the fins 22.

FIG. 14 illustrates a slightly modified version of the fin engaging members and the fins. In the illustrated version of this embodiment shown in FIG. 14, each of the fin engaging members 160, 160 is provided with a longitudinally extending projection 161, 161 that faces generally in a direction toward the back wall of the sheath. The projections 161, 161 are positioned on the shoulders formed at the distal end portions of the fin engaging members 160, 160. In addition, at least two of the fins 122 are provided with a respective recess 123. Each of the projections 161, 161 is adapted to engage the recess 123 in one of the respective fins 122, 122 when the sheath is in the locked cannula covering position. This alternative arrangement provides an additional engagement mechanism between the fin engaging members 160, 160 and the fins 122, 122. In the illustrated version of the embodiment shown in FIG. 14, a recess 123 is provided on each of the oppositely facing surfaces of each fin 122. Providing a pair of recesses 123 on each of the fins 122, as opposed to a single recess on two of the fins, provides greater versatility in that the sheath need not be particularly oriented in one particular position relative to the fins to ensure that the projections 161 engage the recesses 123. Nevertheless, it is to be understood that this additional engagement mechanism can be achieved by providing only one of the fin engaging members 160 with a projection 161 and providing only one of the fins 122 with a recess 123. Other combinations of projections and recesses beyond those described above are also possible. Also, as in the case of other versions of the fin engaging members described above, the fin engaging members 160, 160 shown in FIG. 14 can be angled inwardly slightly towards one another.

The fin engaging members can also take other forms. For example, as shown in FIG. 15, the fin engaging members 260, 260 which are connected to the back wall 254 of the sheath and spaced from the side walls 252, 252 of the sheath can possess a distal end portion configured slightly differently than that illustrated in FIG. 12a. That is, rather than providing a hook-shaped distal end portion defined by a sharply angled shoulder oriented approximately perpendicular to the inner surface of the fin engaging members as depicted in FIG. 12a, the hook-shaped distal end portion can be defined by shoulders 262, 262 that are more gently tapered, although still adequate to engage the fins in a manner sufficient to maintain the sheath in the locked cannula covering position. As in the earlier embodiments, the fin engaging members 260, 260 can once again be angled inwardly slightly toward one another to form an acute included angle with respect to the back wall 254 of the sheath.

FIG. 16 illustrates another alternative for the fin engaging members 360, 360 that are connected to the back wall 354 of the sheath and spaced from the side walls 352, 352 of the sheath. In the version shown in FIG. 16, the fin engaging members 360, 360 are configured to engage respective fins 322, 322 that are shifted approximately 45° relative to the orientation of the fins shown in FIG. 12a. With this orientation of the fins 322, 322 shown in FIG. 16, the distal end portions of the slightly inwardly inclined fin engaging members 360, 360 can be provided with a shoulder that is angled more severely than that illustrated in FIG. 12a so that the shoulders 362, 362 form an acute included angle with respect to the inner surface of the fin engaging members 360, 360. This version of the hook-shaped distal end portions of the fin engaging members 360, 360 helps facilitate engagement with the differently positioned fins 322, 322.

FIG. 17 illustrates another embodiment in which a pair of fin engaging members 460, 460 connected to the back wall 454 of the sheath and spaced from the sidewalls 452, 452 of the sheath engage respective fins 422, 422 of the hub of the needle assembly. In this embodiment, the cannula holding member is provided with three fins 422 spaced apart at equal intervals of 120°. The distal end portion of each of the fin engaging members 460, 460 is configured similar to that described above in connection with the embodiment shown in FIG. 16 so that the hook-shaped distal end portion of each fin engaging member 460, 460 is able to engage the respective fin 422, 422 to lock the sheath in the cannula covering position.

FIG. 18 illustrates a still further embodiment utilizing a single fin engaging member 560. As in the other embodiments, the single fin engaging member 560 is connected to the back wall 554 of the sheath and is spaced from the adjoining sidewall 552 of the sheath. The fin engaging member 560 can also be angled inwardly slightly. In this embodiment, the shoulder 562 on the distal end portion of the fin engaging member 560 is longer than in the other embodiments for purposes of ensuring that the distal end portion of the single fin engaging member 560 is able to sufficiently engage at least one of the fins 522 (or a portion of the fin region of the hub) in a way that locks the sheath in the cannula covering position.

FIG. 19 illustrates a slight variation with respect to the embodiment shown in FIG. 18. In the embodiment shown in FIG. 19, the fins 622 are rotationally offset approximately 45° relative to the orientation of the fins 522 shown in FIG. 18. Once again, the shoulder 662 on the distal end portion of the fin engaging member 660 is sufficiently long to ensure that the distal end portion of the fin engaging ember 660 is able to engage at least one of the fins 622 in a way that maintains the sheath in the locked cannula covering position.

FIGS. 20*a* and 20*b* illustrate a still further embodiment. In this embodiment, the fin engaging members 760, 760 are once again connected to the back wall 754 of the sheath and are spaced from the side walls 752, 752 of the sheath. This embodiment differs from all of the earlier embodiments with respect to the location of the fin engaging members relative to the fins. That is, in the earlier embodiments, the fin engaging members are positioned along the longitudinal sides of the fins (i.e., the fin engaging members engage the fins at a position located between the longitudinal ends of the fins). In the embodiment shown in FIGS. 20*a* and 20*b*, the fin engaging members 760, 760 are positioned at the distal ends of the respective fins so that the fin engaging members 760, 760 engage the distal ends of the fins as best seen in FIG. 20*b*.

In the embodiments of the safety needle assembly described above, the fin engaging members (or fin engaging member) are configured to engage respective fins on the hub of the needle assembly in a way that locks the sheath in the cannula covering position. Other variations on the disclosed embodiments are possible. For example, the fins (fin) can be provided with respective holes that receive an end portion of the respective fin engaging member when the sheath is pivoted to the closed cannula covering position. This engagement of ends of the fin engaging members in holes in the fins can provide an additional measure of engagement for ensuring that the sheath is unable to pivot in a direction away from the cannula after the sheath has reached the locked cannula covering position. Alternatively, the distal end of each fin engaging member can be provided with a hole or opening to receive one of the fins as the sheath is pivoted towards the cannula to achieve the locked cannula covering position.

The various versions of the safety device described above can advantageously be used in connection with a wide variety of cannula holding members that possess fins, so long as the sheath, including the fin engaging members, are appropriately sized to engage the fins or the fin region at which the fins are located. Thus, the configuration of the needle assembly need not be changed or altered to accommodate the safety device. Rather, the safety device merely needs to be sized to engage the fins to achieve the locked cannula covering position described above. Thus, the manufacturing costs associated with outfitting cannula holding members with a safety device can be reduced.

In addition, because the fin engaging member or fin engaging members are spaced from the sidewalls of the sheath, forces applied to the sidewall of the sheath do not directly affect the engagement of the fin engaging member(s) with the respective fin(s). Thus, a non-releasable or permanently locked safety device is achieved that prevents accidental unlocking in the event of an inadvertent application of a force to the sidewalls of the sheath. Also, in all of the embodiments of the fin engaging members (fin engaging member) described above, the fin engaging members (fin engaging member) do not extend outwardly beyond the side walls of the sheath. Thus, the fin engaging members (fin engaging member) are not readily accessible which reduces the possibility that a force tending to override the locked position of the sheath is applied to the fin engaging members (fin engaging member).

The safety device is also designed so that the sheath does not come into contact with the cannula, thus reducing the risk that fluids will splatter or spray as the sheath is being moved to the locked cannula covering position.

The safety device can be configured so that the sheath automatically moves away from the cannula if the sheath is not sufficiently pivoted in the closing direction to cause the fin engaging members (fin engaging member) to lockingly engage the fins (fin). The living hinge described above for connecting the sheath 50 to the collar 42 represents one way of achieving such a result. A living hinge possesses a "memory" of its original position and tends to return to such position after being repositioned by a user. Thus, if the sheath is not sufficiently pivoted to cause the fin engaging members (fin engaging member) to engage the fins (fin) in a way that achieves the locked cannula covering position, the sheath will tend to spring back or move away from the cannula, thus indicating that the sheath has not been sufficiently pivoted into the locked cannula covering position. In connection with the embodiments of the multi-piece hinge described above, a similar result could be achieved by incorporating a resistance feature, such as a spring arm, that the user must overcome to position the sheath in the locked cannula covering position. In this alternative, if the sheath is not sufficiently pivoted to cause the fin engaging members (fin engaging member) to engage the fins (fin) in a way that achieves the locked cannula covering position, the resistance feature (e.g., spring arm) will move the sheath away from the cannula, thus once again indicating that the sheath has not been sufficiently pivoted into the locked cannula covering position.

As mentioned previously, the sheath 50 is pivotally connected to the collar 42 by way of, for example, a living hinge. However, it is also possible to use a multi-piece hinge to pivotally connect the sheath 50 to the collar 42. U.S. Pat. No. 6,719,737, the entire disclosure of which is incorporated herein by reference, discloses one example of a multi-piece hinge for pivotally connecting the sheath 50 to the collar 42. FIG. 21 generally illustrates the multi-part hinge disclosed in the aforementioned patent.

As shown in FIG. 21, the multi-piece hinge includes a first part 90 formed as a part of the collar 42 and a second part 92 formed as a part of the sheath 50. The first part 90 includes a pair of spaced apart mounting ears 91, 91 each provided with a through hole, while the second part 92 is provided with a pair of outwardly extending and axially aligned pins 93. Each of the pins 93 is adapted to be positioned in the through hole in one of the mounting ears 91, 91 so that the second part 92, which is connected to or forms a part of the sheath, is able to pivot relative to the first part 90, which is connected to or forms a part of the collar. As described in the aforementioned patent, the pin mount 94 on which the pins 93 are mounted can also be provided with a plurality of flat surfaces 95. These flat surfaces 95 are adapted to engage a surface 96 on the first part 90 located between the mounting ears 91. As discussed in the aforementioned patent, during pivoting movement of the sheath relative to the collar, the flat surfaces 95 successively engage the surface 96 to produce a desirable clicking feeling for the user. The engagement between the flat surfaces 95 and the surface 96 also causes the sheath 50 to pivot away from the cannula if the sheath 50 has not been pivoted sufficiently to cause the sheath to reach the locked position relative to the cannula, thus providing an indication to the user that the sheath is not in the locked position.

FIG. 22 illustrates an alternative version of a multi-piece hinge. In this embodiment, the first part 190 is provided with a single mounting ear 191 possessing a through hole while the second part 192 is provided with a pair of axially aligned pins 193, 193 mounted on respective pin mounts 194, 194. The first part 190 and the second part 192 are connected to one another by fitting each of the pins 193, 193 in the through hole in the mounting ear 191. The second part 192 which is connected to or forms a part of the sheath can thus pivot relative to the first part 190 which is connected to or forms a part of the collar. The respective pin mounts 194 can once again be provided with flat surfaces 195, 195 that successively engage respective surfaces 196, 196 on the first part 190 during pivoting movement of the sheath relative to the collar to provide, as discussed above, the clicking feeling and an indication that the sheath has not been sufficiently pivoted towards the cannula to reach the locked position.

An alternative version illustrated in FIG. 23 is somewhat similar to the version shown in FIG. 22, except that the second part 292 is provided with a single pin 293 extending from a pin mount 294. In the version shown in FIG. 23, the single pin 293 is longer than the pins illustrated in the FIG. 22 embodiment. The pin 293 is adapted to be positioned in a through hole provided in the mounting ear 291 of the first part 290. Once again, with the pin 293 positioned in the through hole in the mounting ear 291, the second part 292 which is connected to or forms a part of the sheath is able to pivot relative to the first part 290 which is connected to or forms a part of the collar. Also, the pin mount 294 on the second part 292 can be provided with flat surfaces 295 that engage a surface 296 on the first part 290 during pivoting movement of the sheath relative to the collar for the reasons mentioned above and discussed in the aforementioned patent.

A fourth embodiment of the multi-piece hinge is illustrated in FIG. 24 and includes a first part 390 and a second part 392. The first part 390 is provided with a mounting ear 391 that is open along one side to receive a pin 393 extending between two pin mounts 394 on the second part 392. Flat surfaces 395 on the pin mounts 394, 394 of the second part 392 are adapted to successively engage respective surfaces 396, 396 on the first part 390 for the reasons discussed above and in the aforementioned patent.

In the embodiments of the multi-piece hinge described above, the first part is described as being connected to or forming a part of the collar, while the second part is described as being connected to or forming a part of the sheath. This arrangement can be reversed so that the first part is connected to or forms a part of the sheath, while the second part is connected to or forms a part of the collar.

As discussed above, the collar 42 is positioned in the recessed region 26 of the cannula holding member 16. For purposes of proper operation of the safety device so that the fin engaging members (fin engaging member) are able to engage the fins (fin), it is preferable that the collar is rotationally oriented on the cannula holding member in a manner that allows the engagement to occur. One way of achieving the desired orientation is to fix the collar on the cannula holding member in the required position or rotational orientation. The collar can be fixed on the cannula holding member by utilizing a fixing arrangement between the collar and the cannula holding member similar to that illustrated in the aforementioned U.S. Pat. No. 6,719,737. That is, the inner surface of the collar can be provided with teeth or projections that engage similar teeth or projections on the portion of the skirt 24 disposed on the distal side of the recessed region 26.

An alternative rotation fixing arrangement is illustrated in FIG. 25. Here, the inner surface of the collar 42 is provided with at least one inwardly directed tab 43 that engages a corresponding recess in a portion of skirt 24 on the distal side of the recessed region 26. The arrangement of the tab(s) 43 and the recess(es) 45 can also be properly positioned to ensure that the sheath is in a particular position relative to the cannula. That is, the cannula is typically provided with a beveled distal end portion. Some users prefer to have the bevel oriented in a particular position during usage and would prefer that the sheath in the open position not interfere with normal usage. Thus, the tab(s) 43 and the corresponding recess(es) 45 can be positioned to ensure that when the collar is mounted on the hub, the sheath in the open position does not interfere with the user's preference. For example, the collar can be oriented so that the sheath in the open position is disposed to the side when the bevel on the distal end portion of the cannula is facing upwardly.

Another way of positioning the collar 42 relative to the cannula holding member in a desired orientation is illustrated in FIG. 26 and involves configuring both the inner surface of the collar 42 and the outer surface of the portion of the skirt 24 on the distal side of the recessed portion 26 to possess a polygonal shape. The flat surfaces of the mating polygonal shapes are arranged to provide a desired orientation of the collar on the cannula holding member.

It is also possible to provide a mechanism which allows the collar to be rotated when desired, but then fixed in place once the proper positioning of the collar has been achieved. One example involves a ratchet-type rotation mechanism such as shown in FIG. 27. Here, the portion of the skirt 24 on the distal side of the recessed region 26 is provided with a series of bumps or protuberances 47, while the inner surface of the collar 42 is provided with a pair of oppositely positioned recesses 49. When the bumps 47 are not positioned in the recesses 49, the collar is able to swivel or rotate rather freely. On the other hand, once the bumps 47 are positioned in the recesses 49, the collar 42 is rotationally secured in position relative to the hub. Of course, it is possible to provide different numbers of recesses 49 and protuberances 47 than that shown in FIG. 27.

As an alternative ratchet-type rotation mechanism, an arrangement similar to that shown in FIG. 26 could be employed using mating polygonal-shaped surfaces, except that a larger gap would be provided between the polygonal-shaped inner surface of the collar 42 and the polygonal-shaped outer surface of the portion of the skirt 24 on the distal side of the recessed portion 26. This larger gap would allow the collar 42 to flex slightly upon application of a rotational force to the collar (or the sheath), thus allowing the collar 42 to rotate around the cannula holding member 16 until the two polygonal-shaped surfaces once again move into alignment with one another.

As an alternative to the ratchet-type rotation mechanism which allows the collar to be generally rotated in steps or stages, the collar 42 and the portion of the skirt 24 on the distal side of the recessed region 26 can be configured to allow a somewhat smooth swiveling movement or generally continuous rotation of the collar, while still allowing the collar to be fixed at a desired rotational position. This could be accomplished by providing bumps or protuberances on the inner surface of the collar which circumscribe an inner diameter slightly smaller than the outer diameter of the portion of the skirt 24 on the distal side of the recessed portion 26. With such a configuration, the collar 42 could be rotationally adjusted to a desired orientation upon applying sufficient rotational force to the collar 42 (or the sheath). However, once the rotational force is removed, the collar 42 would resist further rotation and thus remain in the desired orientation.

One benefit of the ratchet-type swivel mechanism described above as compared to the smooth swivel mechanism is that the ratchet-type swivel is not as likely to slip out of position while pivoting the sheath towards the cannula. That is, upon pivoting the sheath in the closing direction toward the cannula, a sideways force applied to the sheath could, in the case of a smooth swivel mechanism, cause the collar to rotate. Such a possibility is not as likely to occur in the case of the ratchet-type swivel.

As discussed above in connection with the illustrations in FIGS. 12*a* and 12*b*, the sheath can be provided with a stop rib 70 for preventing further significant pivoting movement of the sheath 50 in the closing direction once the fin engaging members (member) have engaged the fins (fin) to avoid contact of the sheath with the cannula. As also mentioned, the stop rib 70 can be provided with a recess 71 for receiving one of the fins of the hub. This recess can also serve to assist in rotationally orienting the collar on the hub so that the fin engaging members (fin engaging member) are able to engage the fins (fin). In connection with the ratchet-type swivel mechanism, and possibly also the smooth swivel mechanism, as the sheath is pivoted toward the cannula, if the sheath is not quite positioned in the rotational orientation that will allow the fin engaging members (fin engaging member) to smoothly engage the fins (fin), the recess can help guide the sheath into the proper rotational position. For example, by providing inclined sides that lead into the recess as shown in FIGS. 12*a* and 12*b*, the fin(s) will be guided into the recess 71 in a way that rotationally shifts the sheath to the rotational position designed to allow the fin engaging members (fin engaging member) to engage the fins (fin) in a locking manner.

As discussed above, the cannula holding member 16 to which the safety device 40 is assembled is formed in one piece as a part of the fluid transfer device (e.g., syringe). However, it is also possible for the cannula holding member to be configured separate from the fluid transfer device and connectable to the fluid transfer device. FIGS. 28-31 illustrate such an alternative arrangement. The cannula holding member 116 here includes a hub 120 provided with one or more fins 122. The cannula holding member 116 shown in FIGS. 28-31 differs from the earlier described versions of the cannula holding member in that the proximal end of the cannula holding member 116 is provided with a radially outwardly directed flange 117. This flange 117 (e.g., luer fitting) is adapted to be engaged with the distal end of the fluid transfer device, for example a syringe barrel, to connect the cannula holding member 116 to the syringe barrel. This can be accomplished in a known manner such as by engaging the flange 117 with threads on the distal end of the syringe barrel. Alternatively, the cannula holding member can be appropriately configured to be friction fitted to the distal end of the fluid transfer device (e.g., syringe). Generally speaking, in all other respects, the cannula holding member 116 shown in FIGS. 28-31 is the same as described above. In addition, the safety device 40 described above can be used in connection with the cannula holding member shown in FIGS. 28-31.

FIG. 28 illustrates the cannula holding member 116 together with the safety device 40 forming a safety needle assembly. The safety needle assembly can also include the optional protector described above, if used. The safety device 40, comprised of the collar 42 and the sheath 50, is mounted on the cannula holding member 116, with the sheath 50 positioned in the open position in which the cannula 118 is not covered. FIG. 29 depicts the safety needle assembly when the sheath 50 is in the closed cannula covering position. FIGS. 30 and 31 illustrate the safety needle assembly, viewed from the portion of the sheath 50 at which is provided the opening in the sheath, to depict the fin engaging members in engagement with the fins of the hub. The various versions of the fin engaging members described above (generally identified as 60 in FIG. 31) can be employed in connection with the needle assembly shown in FIGS. 28-31. Similarly, the different numbers and arrangements of fins (generally identified as 122 in FIGS. 28 and 31) on the hub as described above are equally applicable in connection with the version of the cannula holding member shown in FIGS. 28-31. Also, the different hinges described above can also be used together with the safety device shown in FIGS. 28-31 to connect the sheath and the collar.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A method of covering a cannula fixed to a cannula holding member, the method comprising:

pivoting a sheath that is pivotally mounted on the cannula holding member, the cannula being fixed to the cannula holding member so that a beveled distal end of the cannula projects beyond a distal end of the cannula holding member, the cannula holding member comprising at least one outwardly directed and longitudinally extending fin;

the sheath comprising an interior bounded by a back wall, a pair of oppositely positioned side walls and an opening positioned opposite the back wall, the opening extending along at least a portion of a longitudinal extent of the sheath;

the sheath also comprising at least one cantilevered fin engaging member connected to the back wall and extending from the back wall of the sheath in the interior in a direction toward the opening, the at least one fin engaging member being spaced from both side walls of the sheath and possessing a distal end portion;

the sheath being pivoted toward the cannula to cause the beveled distal end of the cannula to be positioned in the interior of the sheath and to cause a distal end portion of the at least one cantilevered fin engaging member to engage the at least one fin on the cannula holding member to lock the sheath in a cannula covering position relative to the cannula holding member and prevent the sheath from being pivoted away from the cannula.

2. The method according to claim 1, wherein:

the cannula holding member comprises at least two outwardly directed and longitudinally extending fins; and the sheath comprises two cantilevered fin engaging members connected to the back wall, extending away from the back wall in a direction toward the opening and being positioned in spaced relation to adjacent side walls of the sheath;

the pivoting of the sheath causing the distal end of each fin engaging member to engage one of the fins.

3. The method according to claim 1, wherein:

the sheath is pivotally connected to a collar that is rotatably mounted on the cannula holding member, the method comprising rotating the collar relative to the cannula holding member to adjust a rotational position of the sheath relative to the cannula holding member.

4. The method according to claim 1 wherein the sheath comprises a generally U-shaped cross-section.

5. A method of covering a cannula fixed to a cannula holding member and possessing a distal end, the method comprising:

pivoting a sheath that is pivotally mounted on the cannula holding member, the cannula being fixed to the cannula holding member and possessing a distal end projecting beyond a distal end of the cannula holding member; the cannula holding member comprising at least two fins, each of the fins projecting outwardly away from the cannula holding member and extending along at least a portion of a longitudinal extent of the cannula holding member;

the sheath comprising a back wall, oppositely positioned side walls defining an interior, and an opening positioned along at least a portion of a longitudinal extent of the sheath;

the sheath also comprising at least one arm connected to the back wall of the sheath in the interior and extending in a cantilever manner from the back wall of the sheath in a direction toward the opening, the at least one arm having a distal end portion;

the sheath being provided on the cannula holding member and being pivoted relative to the cannula holding member toward the cannula from one position in which the cannula is exposed to another position in which the sheath covers the cannula and the distal end portion of the at least one arm engages at least one of the fins to prevent the sheath from being pivoted back toward the one position.

* * * * *